(12) United States Patent
Yamasaki et al.

(10) Patent No.: US 9,351,944 B1
(45) Date of Patent: May 31, 2016

(54) MALODOR ELIMINATING COMPOSITIONS

(75) Inventors: Akiko Yamasaki, New Milford, NJ (US); James Buchanan, Mercerville, NJ (US); Michael John Munroe, Ashford Kent (GB)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 683 days.

(21) Appl. No.: 12/615,157

(22) Filed: Nov. 9, 2009

Related U.S. Application Data

(60) Provisional application No. 61/112,282, filed on Nov. 7, 2008.

(51) Int. Cl.
*A61K 31/05* (2006.01)
*A61K 31/11* (2006.01)
*A61K 31/12* (2006.01)

(52) U.S. Cl.
CPC ............... *A61K 31/05* (2013.01); *A61K 31/11* (2013.01); *A61K 31/12* (2013.01)

(58) Field of Classification Search
CPC ........ A61K 31/05; A61K 31/11; A61K 31/12
USPC ...................................................... 424/49–54
See application file for complete search history.

(56) References Cited

U.S. PATENT DOCUMENTS

| | | | |
|---|---|---|---|
| 3,914,227 A | 10/1975 | Pittet et al. | |
| 4,906,488 A | 3/1990 | Pera | |
| 5,580,545 A * | 12/1996 | Washino et al. | ............... 424/49 |
| 5,589,158 A | 12/1996 | Mankoo | |
| 5,739,100 A * | 4/1998 | Horino et al. | .................. 512/25 |
| 6,471,946 B1 | 10/2002 | Takatsuka et al. | |
| 6,491,896 B1 | 12/2002 | Rajaiah et al. | |
| 6,495,176 B1 | 12/2002 | McGenity et al. | |
| 6,723,305 B2 | 4/2004 | DePierro et al. | |
| 6,869,923 B1 | 3/2005 | Cunningham et al. | |
| 7,300,645 B2 | 11/2007 | Takatsuka et al. | |
| 7,332,462 B2 | 2/2008 | McGee et al. | |
| 7,465,697 B1 | 12/2008 | DeAth | |
| 2004/0141927 A1 | 7/2004 | Johnson et al. | |
| 2006/0002876 A1 * | 1/2006 | Cahen | ......................... 424/70.1 |
| 2006/0153959 A1 * | 7/2006 | Behan et al. | .................. 426/534 |
| 2006/0165622 A1 * | 7/2006 | Hiramoto et al. | ............... 424/65 |
| 2006/0222615 A1 * | 10/2006 | Kuroda et al. | ............. 424/70.12 |
| 2007/0149424 A1 * | 6/2007 | Warr et al. | .................... 510/101 |
| 2008/0247966 A1 | 10/2008 | Natsch et al. | |
| 2008/0311054 A1 | 12/2008 | Natsch et al. | |
| 2009/0317536 A1 * | 12/2009 | Cambeen et al. | ............. 426/650 |

FOREIGN PATENT DOCUMENTS

| | | |
|---|---|---|
| EP | 0404470 | 6/1990 |
| EP | 1 561 476 A1 | 8/2005 |
| JP | 2004-155681 A | 6/2004 |
| JP | 2005-187394 A | 7/2005 |
| JP | 2006-121958 A | 5/2006 |
| JP | 2009-179711 A | 8/2009 |
| WO | WO2007/007978 | 1/2007 |
| WO | WO2007/071085 | 6/2007 |
| WO | WO 2008/005548 A2 | 1/2008 |
| WO | WO2008/026140 | 3/2008 |
| WO | WO 2008/135746 A2 | 11/2008 |

OTHER PUBLICATIONS

"Damascenone" (SciFinder. CAS Registry No. 23726-93-4:_ Damascenone). Accessed Jun. 12, 2013.*
Hoda H. M. Fadel (Journal of Islamic Academy of Sciences 4:3, 196-199, 1991).*
Liu X. CN102150941. (2011) English abstract.*
Honda Hideo et al. CN 103142430. (2013) English abstract.*
Annex to the Invitation to Pay Additional Fees dated Jan. 14, 2016 in International Application No. PCT/IB2015/001677.
International Search Report and Written Opinion dated Mar. 23, 2016 in International Application No. PCT/IB2015/001677.

* cited by examiner

*Primary Examiner* — Jeffrey S Lundgren
*Assistant Examiner* — Chris Simmons
(74) *Attorney, Agent, or Firm* — Baker Botts L.L.P.

(57) ABSTRACT

The present invention provides malodor eliminating compositions that ameliorate undesirable sensations (e.g., undesirable sensations due to presence of sulphur-containing compounds) when added to foods, beverages, toothpastes, mouthwashes and other orally consumable products and consumed (e.g., when bucally administered in a consumer product).

19 Claims, 7 Drawing Sheets

MALODOR ELIMINATING COMPOSITIONS

CROSS REFERENCE TO RELATED APPLICATIONS

The present application claims the benefit of U.S. Ser. No. 61/112,282, filed Nov. 7, 2008, which is hereby incorporated herein by reference in its entirety.

FIELD OF THE INVENTION

The present invention relates to compositions that ameliorate undesirable sensations (e.g., undesirable sensations due to the presence of sulphur-containing compounds) when added to foods, beverages, toothpastes, mouthwashes and other orally consumable products and consumed (e.g., when bucally administered in a consumer product).

BACKGROUND OF THE INVENTION

It is known that various materials may alleviate oral malodor, which impart undesirable tastes to orally consumed products. These materials include, for example, antibacterial agents, natural extracts with or without an enzyme component, antioxidants, chelating agents, and fragrance and flavor materials. Other substances which are known to control oral malodor include quaternary ammonium, triclosan, baking soda, cetylpyridinium chloride, cyclohexidine, zinc salts, stannous salts, antibacterial flavor materials, essential oils, and natural extracts. These materials can provide an oral malodor suppression effect in various ways when applied to the oral cavity, e.g., by preventing malodor generation, by chemically reacting with malodor materials, or by simply masking the malodor.

U.S. Published Patent Application No. 2008/0311054 A1 describes oral malodor counteracting compositions using unsaturated alkanoic acid esters, which purportedly inhibit the enzyme that produces oral bacteria. Similarly, U.S. Published Patent Application No. 2008/0247966A1 relates to an oral malodor counteracting composition that is based on bacteria enzyme inhibition.

International Published Application No. WO 2007/071085 describes oral malodor counteracting compositions that include esterified fumarates, which purportedly chemically bind to the malodor molecules. Many materials used in the prior art, however, can cause unpleasant effects like astringency, or a metallic taste; or are unstable in the orally consumed product. Also compositions that merely mask malodor only reduce malodor perception; they do not eliminate the malodor, which persists in the oral cavity. Therefore, there remains a need for improved compositions that can reduce malodor materials in orally consumed products.

SUMMARY OF THE INVENTION

The present invention provides malodor eliminating compositions that provide efficient malodor elimination (e.g., malodor caused by sulphur-containing and amine-containing compounds).

In one embodiment, the malodor eliminating composition includes at least one "Group A" malodor eliminating compound and at least one "Group B" malodor eliminating compound. In certain embodiments, the combination of a Group A malodor eliminating compound and a Group B malodor eliminating compound provides surprising and/or synergistically increased malodor elimination.

In one embodiment, Group A malodor eliminating compounds include at least one compound selected from compounds that contain a carbonyl functional group and a carbon-carbon double or triple bond at the α, β carbons (with respect to the carbonyl group). The double or triple carbon-carbon bond may be found along an aliphatic hydrocarbon chain, or within a cycloalkyl carbon ring, such as within a 5-membered or 6-membered carbon ring (such as the double bound in piperitone).

In one embodiment, Group B compounds are selected from a) phenolic compounds; b) compounds represented by Formula I:

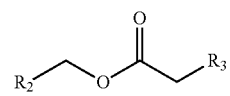

wherein $R_2$ and $R_3$ are independently selected from H or an aliphatic linear or branched, saturated or unsaturated carbon chain containing from 1 to 8 carbon atoms; and c) compounds represented by Formula II:

wherein $R_4$ is an aliphatic linear or branched, saturated or unsaturated carbon chain containing from 5 to 9 carbon atoms.

In one embodiment, Group B compounds are selected from eugenol, isoeugenol, 3-hexenyl alcohols (e.g., cis-3-hexanol) and 3-hexenyl esters (e.g., cis-3-hexenyl acetate).

In another embodiment, a composition is provided that includes at least one malodor eliminating compound (e.g., a Group A or Group B compound) and at least one malodor masking compound (e.g., ethyl butyl, menthol, and/or anisyl acetate). In yet another embodiment, a composition is provided that includes at least one Group A malodor eliminating compound, at least one Group B malodor eliminating compound, and at least one malodor masking compound. In further embodiments, the foregoing composition further includes a solvent suitable for use in orally consumed products (e.g., foods, beverages, tooth pastes, mouthwashes).

The present invention also provides methods of reducing malodor that comprises adding a composition of the present invention to an orally consumed product.

BRIEF DESCRIPTION OF THE DRAWINGS

For a more complete understanding of various embodiments of the described subject matter and its advantages, reference is now made to the following description, taken in conjunction with the accompanying drawings, in which.

DETAILED DESCRIPTION

Figure 1:
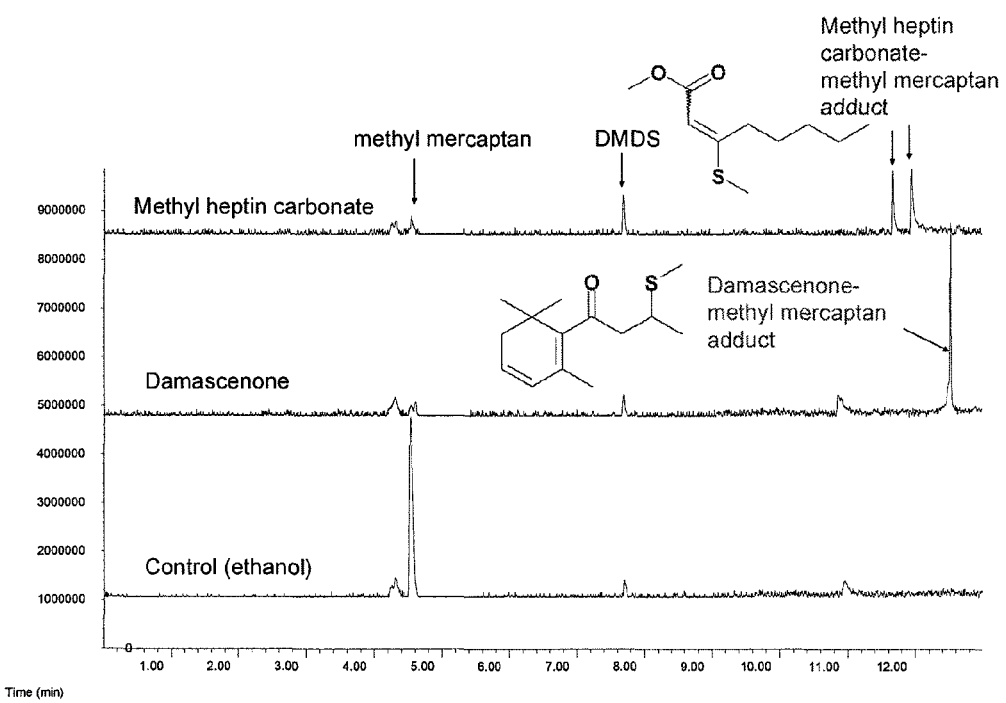
FIG. 1 depicts a GC-PFPD (Gas Chromatography-Pulsed Flame Photometric Detector) analysis of reaction products of a malodor test material and certain malodor eliminating compounds according to some embodiments of the disclosed subject matter.

As used herein, a "malodor eliminating compound" or a "malodor eliminating material" refers to a compound that facilitates at least partial removal of malodor-causing materials via chemical reaction with the malodor-causing constituent, as opposed to a material that simply masks (i.e., covers up) the perception of a malodor. In certain embodiments, malodor-causing constituents react with the malodor eliminating compound(s) to form at least one new compound that is more hedonically pleasing, or at least less hedonically displeasing. In certain embodiments, malodor eliminating compositions and materials posses specific chemical functional groups that are prone to reaction with a variety of malodor-causing constituents, especially malodor-causing constituents, including thiols and amines.

As used herein, the phrase "malodor masking compound" refers to a compound that masks the perception of a malodor, thereby providing a hedonically pleasing perception to the consumer of an orally consumed product, or otherwise rendering the product to which it is applied (e.g., an orally consumed consumer product) more hedonically appealing, or less hedonically displeasing.

As used herein, a "malodor eliminating composition" refers to a composition containing at least one malodor eliminating compound and optionally further includes a malodor masking compound and/or a solvent (e.g., a diol solvent like propylene glycol). Specific malodor eliminating compositions are described herein.

As used herein, the phrase "consumer product" or "end product" refers to composition that is in a form ready for use by the consumer for the marketed indication. A mouthwash consumer product refers to a consumer product that is indicated for oral and/or buccal use for improving oral hygiene (e.g., to ameliorate halitosis and/or dental plaque). Such products must be in a form suitable for human oral and/or buccal administration (e.g., as a gargle or rinse).

In this regard, the compositions disclosed in U.S. Pat. No. 7,465,697, for example, which are indicated to be used as household cleaning and disinfecting agents, are ill-suited for use in a mouthwash consumer product.

As used herein, a "solvent suitable for use in a consumer product" is a solvent that, when combined with other components of an end product, will not render the end product unfit for its intended consumer use. Thus, for example, a solvent suitable for use in a mouthwash must be one that does not compromise the ability of the end product to be orally consumed as indicated (e.g. gargled, rinsed and/or swallowed).

As used herein, the term "C log P" refers to the calculated n-octanol/water partition coefficient, as calculated by "Molecular Modeling Pro" software, (version 6.0.6) available from Chem SW, Fairfield, Calif. Additional details regarding C log P values can be found in U.S. Pat. No. 6,869,923 at col. 3, ll. 18-38, which is hereby incorporated by reference in its entirety.

Group A Compounds

In one embodiment Group A malodor eliminating compounds are selected from compounds that contain a carbonyl functional group and a carbon-carbon double or triple bond at the α, β carbons (with respect to the carbonyl group). The double or triple carbon-carbon bond may be found along an aliphatic hydrocarbon chain, or within a cycloalkyl carbon ring, such as within a 5-membered or 6-membered carbon ring (such as the double bound in piperitone).

In one embodiment, Group A compounds are represented by the Formula III or IV:

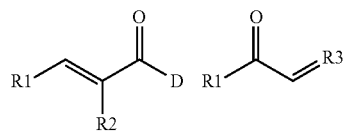

wherein $R_1$ is selected from $C_4$-$C_8$ saturated or unsaturated cycloalkyl, a $C_4$-$C_8$ saturated or unsaturated cycloalkyl that is optionally uni-substituted or di-substituted, tri-substituted, or tetra-substituted with a $C_1$-$C_3$ alkyl group at any carbon atom as permitted by valency; hydroxy; acetate; a $C_1$-$C_3$ alkyoxy group; a benzyl group that is optionally uni-substituted or di-substituted with $C_1$-$C_3$ alkyl groups at any carbon atom as permitted by valency; and a saturated or unsaturated, linear or branched $C_2$-$C_9$ alkyl group;

$R_2$ is selected from a hydrogen; and a branched or linear chained $C_1$-$C_6$ alkyl group;

D is selected from a hydrogen; a branched or liner chained $C_1$-$C_6$ alkyl group, and a $C_1$-$C_6$ a linear or branched alkoxy group.

$R_3$ is selected from hydrogen; a branched or linear chained $C_1$-$C_4$ alkyl group.

In one embodiment, $R_1$ in Formula III or IV is a saturated $C_6$ cycloalkyl group. In another embodiment, $R_1$ is selected from a linear or branched chain $C_1$-$C_9$ alkyl group, and a linear or branched chain $C_2$-$C_9$ alkenyl group.

In another embodiment, $R_1$ in Formula III or IV is selected from the groups represented by the formula:

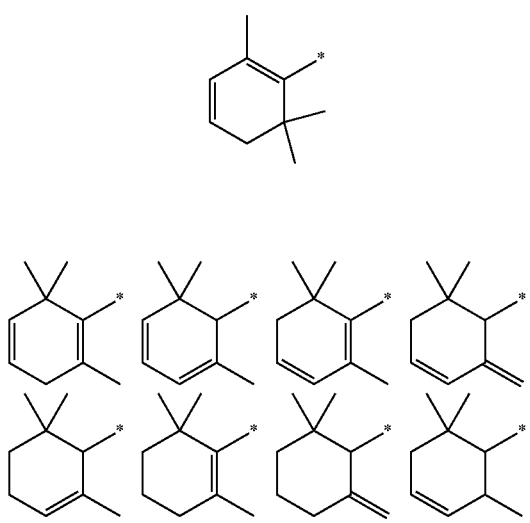

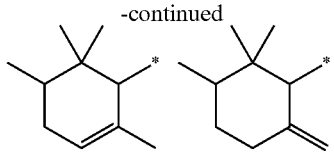

wherein * represents the attachment to the rest of the molecule as represented by Formula III or IV.

In another embodiment, $R_1$ in Formula III or IV is an unsubstituted benzyl group.

In another embodiment, $R_1$ in Formula III or IV is represented by the formula:

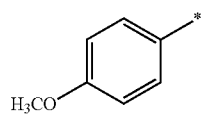

wherein * represents the attachment to the rest of the molecule in Formula III or IV.

In one embodiment, Group A compounds can further include compounds represented by the Formula V:

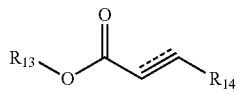

wherein
$R_{13}$ is selected from a $C_1$-$C_2$ alkyl group;
$R_{14}$ is selected from a $C_1$-$C_9$ alkyl group; and
the dashed line represents an optional triple bond. Hence, in one embodiment, the α, β carbons (with respect to the carbonyl group) are bound by a double bond. In another embodiment, the α, β carbons (with respect to the carbonyl group) are bound by a triple bond.

In one embodiment of the present invention, the malodor eliminating composition includes at least one Group A compound selected from 2-cyclopentene-1-one and 2-cyclohexene-1-one. The 2-cyclopentene-1-one and 2-cyclohexene-1-one may optionally be substituted with a linear or branched chain $C_1$-$C_6$ alkyl group, or a linear or branched chain $C_1$-$C_6$ alkenyl group at any carbon atom, as permitted by valency.

In another embodiment, the malodor eliminating composition includes at least one Group A compound selected from methyl heptin carbonate and methyl octin carbonate. In an alternative embodiment, methyl heptin carbonate and/or methyl octin carbonate are excluded as a Group A compound.

In one embodiment of the present invention, the Group A compound includes at least one compound selected from damascenone, damascone beta, damascone alpha, ionone alpha, ionone beta, cinnamic aldehyde, ethyl cinnamate, methyl cinnamate, trans-2-hexenal, trans-2-cis-2-nonadien-1-al, trans-2-trans-4-nonadien-1-al, methyl heptin carbonate, ethyl-trans-2-butenoate, carvone, and piperitone.

In one embodiment of the present invention, the malodor eliminating composition includes at least one Group A compound selected from cinnamic aldehyde, damascenone α, damascenone β, methyl heptin carbonate, and ethyl-trans-2-butenoate.

In one embodiment, the malodor eliminating composition includes at least one Group A compound selected from cinnamic aldehyde and damascenone β.

In one embodiment, the malodor eliminating composition includes at least one Group A compound that has a C log P of 5.0 or lower. In one embodiment, the malodor eliminating composition includes at least one Group A compound that has a C log P of 4.0 or lower.

In one embodiment of the malodor eliminating composition, at least one of benzaldehyde, anisaldehyde, methyl heptin carbonate, beta ionone, and beta cyclo citral is excluded as a Group A compound. In one embodiment, methyl heptin carbonate is excluded as a Group A compound only when a Group B compound includes eugenol or iso-eugenol. In one embodiment, beta ionone is excluded as a Group A component only when a Group B component includes methyl 3-hexenoate.

Group B Compounds

In one embodiment, Group B compounds are selected from a) phenolic compounds; b) compounds represented by the Formula I:

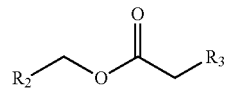

wherein $R_2$ and $R_3$ are independently selected from H or an aliphatic linear or branched, saturated or unsaturated carbon chain containing from 1 to 8 carbon atoms; and c) compounds represented by the Formula II:

wherein $R_4$ is an aliphatic linear or branched, saturated or unsaturated carbon chain containing from 5 to 9 carbon atoms.

In one embodiment, Group B compounds are represented by the Formula VI:

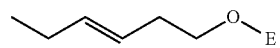

wherein E is selected from hydrogen, and a —(C(O)—$C_1$-$C_6$ linear or branched chain alkyl) group.

In one embodiment, the malodor eliminating composition includes at least one Group B compound selected from eugenol, isoeugenol, 3-hexenyl alcohols (e.g., cis-3-hexanol) and 3-hexenyl esters (e.g., cis-3-hexenyl acetate).

In one embodiment, the malodor eliminating composition includes at least one Group B compound that has a C log P of 4.0 or lower. In one embodiment, the malodor eliminating composition includes at least one Group B compound that has a C log P of 3.0 or lower.

In one embodiment of the malodor eliminating composition, methyl-3-hexenoate is excluded as a Group B compound. In another embodiment, eugenol and iso-eugenol are excluded as a Group B compound. In yet another embodiment, methyl-3-hexenoate is excluded as a Group B compound when beta-ionone and/or methyl heptin carbonate is included as a Group A compound.

Malodor Masking Compounds

In one embodiment, a malodor eliminating composition includes at least one Group A compound and/or at least one Group B compound; and at least one malodor masking compound.

In one embodiment, the malodor eliminating composition includes at least one or more malodor masking compounds selected from ethyl butyl, menthol, anisyl acetate, ethyl acetate, phenethyl alcohol, ethyl 2-methyl butyrate, ethyl butyrate, propylene glycol, citrus oils, peppermint oil, spearmint oil, oil of wintergreen, cinnamon, and ginger.

Solvents

In certain embodiments of the present invention, the malodor eliminating composition includes at least one or more diol solvents. In one embodiment, the diol solvent is selected from 3-(1-menthoxy)propane-1,2-diol (commercially available from Takasago Int'l Corp), p-menthane-3,8-diol (commercially available from Takasago Int'l Corp.), propylene glycol, ethylene glycol, diethylene glycol, ethylene glycol dimethylether, and diethylenegylcol dimethylether.

In one embodiment, the diol solvent is selected from 3-(1-menthoxy)propane-1,2-diol, p-menthane-3,8-diol, and propylene glycol. In one embodiment, the solvent is propylene glycol.

Malodor Eliminating Compositions

In one embodiment, a malodor eliminating composition of the present invention includes at least one Group A compound, and at least one Group B compound. In certain embodiments, the malodor eliminating composition further includes a solvent suitable for use in a consumer product (e.g., a solvent suitable for use in a mouthwash). In one embodiment, a malodor eliminating composition of the present invention includes at least one Group A compound, and at least one Group B compound and a diol solvent, such as one or more of the diol solvents described above.

In one embodiment, the malodor eliminating compositions include at least one Group A compound or at least one Group B compound (or both a Group A compound and a Group B compound) and at least one malodor masking compound.

In one embodiment, the malodor eliminating compounds present in the malodor eliminating composition (i.e. the compounds represented by Group A and/or Group B compounds) are sufficiently hydrophilic that they can react with malodor causing constituents such as a thiol and an amine in a polar environment, for example when present in a water, alcohol, or diol solvent (e.g., propylene glycol). Therefore the malodor eliminating compositions are particularly suitable for the malodor elimination in the aqueous environment, such as oral cavity.

Thus, in certain embodiments, the malodor eliminating compositions of the present invention are combined with a suitable solvent and used in (e.g., in creating) a mouthwash or other oral personal care product. The malodor eliminating compounds and malodor masking compounds impart to the oral care products pleasant effects in the end products that consumers generally find hedonically pleasing.

In certain embodiments, the malodor eliminating composition includes one or more of the following Group A compound/Group B compound pairings (i.e., the malodor eliminating composition includes the following two compounds): ethyl cinnamate/hexenyl-cis-3-acetate; trans-2-hexenal/hexenyl-cis-3-acetate; damascenone/eugenol; cinnamic aldehyde/eugenol; ethyl cinnamate/eugenol; ethyl cinnamate/eugenol; trans-2-hexenal/eugenol; heptadienone/eugenol; and trans-2-hexenal/thymol; cumin aldehyde/eugenol; acetophenone/eugenol.

In one embodiment, the malodor eliminating composition includes one or more of the following Group A or B compound/solvent pairings (i.e, the malodor eliminating composition includes the following two compounds): damascenone/3-(1-menthoxy)propane-1,2-diol; damascone, beta/3-(1-menthoxy)propane-1,2-diol; cinnamic aldehyde/3-(1-menthoxy)propane-1,2-diol; trans-2 hexenal/3-(1-menthoxy)propane-1,2-diol; methyl heptin carbonate/3-(1-menthoxy)propane-1,2-diol; methyl heptadienone/3-(1-menthoxy)propane-1,2-diol; eugenol/3-(1-menthoxy)propane-1,2-diol; thymol/3-(1-menthoxy)propane-1,2-diol; hexenyl cis-3 acetate/3-(1-menthoxy)propane-1,2-diol; cis-3-hexenol/3-(1-menthoxy)propane-1,2-diol; damascenone/propylene glycol; damascone, beta/propylene glycol; cinnamic aldehyde/propylene glycol; trans-2 hexenal/propylene glycol; methyl heptin carbonate/propylene glycol, methyl heptadienone/propylene glycol; eugenol/propylene glycol; thymol/propylene glycol; hexenyl cis-3 acetate/propylene glycol; cis-3-hexenol/propylene glycol; damascenone/p-menthane-3,8-diol; damascone, beta/p-menthane-3,8-diol; cinnamic aldehyde/p-menthane-3,8-diol; trans-2 hexenal/p-menthane-3,8-diol; methyl heptin carbonate/p-menthane-3,8-diol, methyl heptadienone/p-menthane-3,8-diol; p-menthane-3,8-diol/propylene glycol; thymol/p-menthane-3,8-diol; hexenyl cis-3 acetate/p-menthane-3,8-diol; cis-3-hexenol/p-menthane-3,8-diol.

In one embodiment, the malodor eliminating composition includes at least one Group A compound and two Group B compounds, wherein the first Group B compound, $B_1$, is selected from those Group B compounds having a substituted phenol structure (e.g., eugenol, isoeugenol, methyl eugenol and thymol) and the second Group B compound, $B_2$, is selected from those Group B compounds having a linear unsaturated alkyl ester, or alcohol structure.

Accordingly, one embodiment of the present application includes at least one Group A compound, at least one $B_1$ compound, and at least one $B_2$ compound, as selected from the Group A, Group $B_1$ and Group $B_2$ compounds shown in the Table below:

| Group A (alpha, beta, unsaturated carbonyl) | Group $B_1$ (phenolic) | Group $B_2$ (liner unsaturated alkyl ester, alcohol) |
|---|---|---|
| DAMASCENONE | EUGENOL | HEXENYL CIS 3 ACETATE |
| DAMASCONE, BETA | ISOEUGENOL | HEXENYL BUTY, CIS-3, |
| IONONE-ALPHA | METH EUGENOL | HEXENYL PROP, CIS-3, |
| IONONE-BETA | THYMOL | HEXENYL-TRANS-2 ACETATE |
| IRALIA | CARVACROL | HEXENYL CIS 3 ACETATE |
| METHYL ALPHA-IONONE | GUAIACOL | HEXENYL PROP, CIS-3, |
| METHYL-GAMMA-IONONE | CREOSOL | HEXENYL BUTY, CIS-3, |
| CINN ALD | 4-ETHYL GUAIACOL (4-EG) | HEXENYL ISO VAL, CIS-3, |
| AMYL CINN ALD, ALPHA | | HEXENOL, CIS-3- |
| HEXYL CINN ALD | | HEXENOL T2 |
| ETH CINNNAMTE | | 4-HEXEN-1-OL |
| METH CINNAMATE | | NONENOL, CIS 6 |

| Group A (alpha, beta, unsaturated carbonyl) | Group B$_1$ (phenolic) | Group B$_2$ (liner unsaturated alkyl ester, alcohol) |
| --- | --- | --- |
| ISOPROPYL CINNAMATE | | OCTEN-1 3-OL |
| ISOAMYL CINNAMATE | | NONADIENOL, CIS-3, CIS-6, |
| HEXENAL, TRANS-2, | | NONADIENOL, 2,6 |
| HEPTENAL-TRANS-2 | | METHYL-3-NONENOATE |
| DECENAL, TRANS-2, | | PRENYL ACET |
| NONENAL, TRANS-2, | | ETHYL TRANS-3-HEXENOATE |
| OCTENAL T-2 | | |
| DODECENAL, TRANS-2, | | |
| TRIDECENAL, TRANS-2 | | |
| HEPTADIENAL, TRANS-2-TRANS-4 | | |
| NONADIEN-1-AL, TRANS-2, CIS-6, | | |
| NONADIENAL-T-2-T-4 | | |
| CITRAL | | |
| METH 2-PHEN 2-HEXENAL, 5, | | |
| METHYL HEP CARB | | |
| ETH DECADIENOATE | | |
| ETHYL-TRANS-2 BUTENOATE | | |
| PHEN ETH TIGLATE | | |
| METHYL OCT CARB | | |
| 2-Nonenoic acid, methyl ester | | |
| Methyl 2-Hexenoate | | |
| METHYL HEPTADIENONE | | |
| ISO JASMONE | | |
| JASMONE, CIS | | |
| CARVONE-L | | |
| PERILLA ALD | | |
| PIPERITONED | | |
| ISOPHORONE | | |
| PULEGONE | | |
| DAMASCONE ALPHA | | |

In certain embodiments, the malodor eliminating composition includes one or more of the following triple combinations of compounds (i.e., the malodor eliminating composition includes the following triple combinations of a) Group A compounds/b) Group B1 compounds/c) Group B2 compounds): damascenone/eugenol/hexenyl cis-3 acetate; damascenone/eugenol/cis-3-hexenol; damascenone/thymol/hexenyl cis-3 acetate; damascenone/thymol/cis-3-hexenol; damascenone/eugenol/hexenyl cis-3 acetate; damascenone/eugenol/cis-3-hexenol; damascenone/thymol/hexenyl cis-3 acetate; damascenone/thymol/cis-3-hexenol; damascone beta/eugenol/hexenyl cis-3 acetate; damascone beta/eugenol/cis-3-hexenol; damascone beta/thymol/hexenyl cis-3 acetate; damascone beta/thymol/cis-3-hexenol; damascone beta/eugenol/hexenyl cis-3 acetate; damascone beta/eugenol/cis-3-hexenol; damascone beta/thymol/hexenyl cis-3 acetate; damascone beta/thymol/cis-3-hexenol; cinnamic aldehyde/eugenol/hexenyl cis-3 acetate; cinnamic aldehyde/eugenol/cis-3-hexenol; cinnamic aldehyde/thymol/hexenyl cis-3 acetate; cinnamic aldehyde/thymol/cis-3-hexenol; cinnamic aldehyde/eugenol/hexenyl cis-3 acetate; cinnamic aldehyde/eugenol/cis-3-hexenol; cinnamic aldehyde/thymol/hexenyl cis-3 acetate; cinnamic aldehyde/thymol/cis-3-hexenol; trans-2-hexenal/eugenolhexenyl cis-3 acetate; trans-2-hexenal/eugenol/cis-3-hexenol; trans-2-hexenal/thymol/hexenyl cis-3 acetate; trans-2-hexenal/thymol/cis-3-hexenol; trans-2-hexenal/eugenol/hexenyl cis-3 acetate; trans-2-hexenal/eugenol/cis-3-hexenol; trans-2-hexenal/thymol/hexenyl cis-3 acetate; trans-2-hexenal/thymol/cis-3-hexenol; methyl heptin carbonate/eugenol/hexenyl cis-3 acetate; methyl heptin carbonate/eugenol/cis-3-hexenol; methyl heptin carbonate/thymol/hexenyl cis-3 acetate; methyl heptin carbonate/thymol/cis-3-hexenol; methyl heptin carbonate/eugenol/hexenyl cis-3 acetate; methyl heptin carbonate/eugenol/cis-3-hexenol; methyl heptin carbonate/thymol/hexenyl cis-3 acetate; methyl heptin carbonate/thymol/cis-3-hexenol; methyl heptadienone/eugenol/hexenyl cis-3 acetate; methyl heptadienone/eugenol/cis-3-hexenol; methyl heptadienone/thymol/hexenyl cis-3 acetate; methyl heptadienone/thymol/cis-3-hexenol; methyl heptadienone/eugenol/hexenyl cis-3 acetate; methyl heptadienone/eugenol/cis-3-hexenol; methyl heptadienone/thymol/hexenyl cis-3 acetate; methyl heptadienone/thymol/cis-3-hexenol.

As understood by the skilled flavorist, the total amount of the malodor eliminating composition present in a given end product can vary depending on the end product to which it is added, and the taste profile desired by the skilled flavorist. It is also likely that the different amounts of malodor eliminating compounds can be used depending on the end product they are incorporated into (e.g., a mouthwash, toothpaste, gel or gum).

In certain embodiments of the malodor eliminating compositions, the total amount of the Group A compound(s) is from about 0.001% to about 100%, based on the total weight of the malodor eliminating composition, and/or the total amount of the Group B compound(s) is from about 0%, or 0.001% to about 99%, based on the total weight of the malodor eliminating composition.

In other embodiments, the total amount of the Group A compounds is from about 20% to about 95% based on the total weight of the malodor eliminating composition, and/or the total amount of the Group B compounds is from about 2% to about 40%, based on the total weight of the malodor eliminating composition.

In one embodiment, the total malodor eliminating composition is from about 0.01% to about 3.0% of the final product, or from about 0.05% to 1% of the final product. As understood by a person of ordinary skill in the art, the total amount of the malodor eliminating composition present in the main product can vary depending on the consumer product to which it is added, and the taste profile desired by the skilled flavorist.

In one embodiment, for a mouthrinse consumer product, total amount of the Group A compound(s) is from about 0.0001% to about 100%, based on the total weight of the malodor eliminating composition and/or the total amount of the Group B compound(s) is from about 0.0001% to about 99%, based on the total weight of the malodor eliminating composition. In one embodiment, the total use level of the malodor eliminating composition is from about 0.0001% to about 3.0%, based on the total weight of the end product.

In one embodiment, for a toothpaste consumer product, the total amount of the Group A compounds is from about 0.0001% to about 100%, based on the total weight of the malodor eliminating composition, and/or from about 0.0001% to about 99.0% of Group B compounds, based on the total weight of the malodor eliminating composition. In one embodiment, the total amount of the malodor eliminating composition in the end product is from 0.001% to about 5.0% or 6.0%, based on the total weight of the toothpaste end product. As understood by the skilled flavorist, these amounts can vary depending on the specific flavor and product. It is also likely that the different combinations of malodor eliminating agents could result in higher or lower use levels depending on the application and the toothpaste formulation (e.g. whether it is a toothpaste or in the form of a gel).

In another embodiment, for a consumer product suitable for use as chewing gum, the total amount of Group A compounds can be from 0.0001% to about 99.0% (e.g., 0.0001 or 1% to 3%), based on the total weight of the malodor eliminating composition, and/or the total amount of Group B compounds can be from 0.0001% to about 99.0% (e.g., 0.0001 or 1% to 3%), based on the total weight of the malodor eliminating composition.

In another embodiment, for a consumer product suitable for use as a dental floss, the total amount of the Group A compounds is from about 0.0001% to about 100%, based on the total weight of the malodor eliminating composition, and/or from about 0.0001% to about 99.0% of Group B compounds, based on the total weight of the malodor eliminating composition.

In one embodiment, the total amount of the flavor eliminating composition in the dental floss end product is from 0.001% to about 10.0%, based on the total weight of the dental floss formulation end product. As understood by a person of ordinary skill in the art, the total amount of malodor eliminating composition in the end product could vary higher or lower depending on the specific flavor and product and processing.

In one embodiment, a malodor eliminating composition includes at least one of the following compounds: menthol, a dodecalactone (e.g. dodecalactone delta), a decalactone (e.g. dodecalactone delta), ethyl acetate, trans-2-hexenol, at least one ionone (e.g. ionone alpha and/or ionone beta), phenyl ethyl propionate, a phenethyl alcohol (e.g. phenethyl alcohol beta), ethyl 2-methylbutyrate, ethyl butyrate, a undecalactone (e.g. undecalactone gamma), cyclopentadecanolide, damascenone, damascone beta, euguenol, cinnamic aldehyde, a piperitone (e.g. piperitone-d), cis-3-hexanol, cis-3-hexenyl acetate, methyl heptin carbonate, a carvone (e.g. carvone-l), and a propylene glycol solvent.

In one embodiment, a malodor eliminating composition includes at least one of the following compounds: menthol, anethol, peppermint oil, eugenol, cinnamic aldehyde, a piperitone (e.g. piperitone-d), a carvone (e.g. carvone-l), damascenone, a damascone (e.g., damascone beta), ionone, and a distributed medium chain triglyceride solvent.

In one embodiment, the malodor eliminating composition does not include thyme oil and/or a salt of a transition metal.

In one embodiment, a mouthwash consumer product is provided, and the mouthwash consumer product does not include a W/O emulsion phase that includes monoglyceride as a main base a polyol, and/or a polymer. Thus, in one embodiment, the mouthwash consumer product does not include the compositions disclosed in International Published Application No. WO 2007/007978, which is hereby incorporated herein by reference in its entirety.

In one embodiment, a mouthwash consumer product is provided, and the mouthwash consumer product does not include Erospicata oil. In one embodiment, a mouthwash consumer product is provided, and the mouthwash consumer product does not include Erospicata oil and/or a cooling agent. Thus in one embodiment, the mouthwash consumer product does not contain a composition disclosed in U.S. Published Application No. 2004141927, which is hereby incorporated herein by reference in its entirety.

In one embodiment, a mouthwash consumer product is provided, and the mouthwash consumer product does not include a compound represented by the Formula VII:

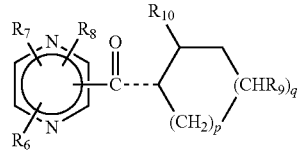

which is disclosed in U.S. Pat. No. 3,914,227, col. 3, lines 29-34, and where $R_6$, $R_7$ and $R_8$ are the same or different and each is hydrogen or methyl; $R_9$ and $R_{10}$ are the same or different and each is hydrogen or lower alkyl; and wherein p is an integer of from 2 up to 5 and q is 0 or 1. Accordingly, in one embodiment, the mouthwash composition does not contain a composition disclosed in U.S. Pat. No. 3,914,227, which is hereby incorporated herein by reference in its entirety.

In some embodiments, a mouthwash consumer product is provided, and the mouthwash consumer product does not include a polyvinylpyrrolidone, cyclodextrin, algin, chitin, or a monomer or derivative thereof. Accordingly, in some embodiments, the mouthwash composition does not contain a composition disclosed in U.S. Pat. No. 4,906,488, which is hereby incorporated herein by reference in its entirety.

In one embodiment, a mouthwash consumer product is provided, and the mouthwash consumer product does not include a flavor enhancing compound such as benzyl benzoate, neryl acetate, and one of the additional compounds described in col. 2, lines 32-39 of U.S. Pat. No. 5,589,158, which is hereby incorporated herein by reference in its entirety. Accordingly, in some embodiments, the mouthwash composition does not contain a composition disclosed in U.S. Pat. No. 5,589,158, which is hereby incorporated herein by reference in its entirety.

In one embodiment, a mouthwash consumer product is provided, and the mouthwash consumer product does not include a tooth remineralization enhancing ingredient such as palatinit, as described in U.S. Pat. No. 6,471,946, which is hereby incorporated herein by reference in its entirety. Accordingly, in some embodiments, the mouthwash composition does not contain a composition disclosed in U.S. Pat. No. 6,471,946, which is hereby incorporated herein by reference in its entirety.

In one embodiment, a mouthwash consumer product is provided, and the mouthwash consumer product does not include a polytutene, an effertutene generator, or an inorganic persalt bleaching agent. Accordingly, in some embodiments, the mouthwash composition does not include a composition disclosed in U.S. Pat. No. 6,491,896, which is hereby incorporated herein by reference in its entirety.

In one embodiment, a mouthwash consumer product is provided, and the mouthwash consumer product does not include a plant extract as described at e.g., col. 3, lines 37-48 and elsewhere of U.S. Pat. No. 6,495,176, which is hereby incorporated herein by reference in its entirety. Accordingly, in some embodiments, the mouthwash composition does not contain a composition disclosed in U.S. Pat. No. 6,495,176, which is hereby incorporated herein by reference in its entirety.

In one embodiment, a mouthwash consumer product is provided, and the mouthwash consumer product does not include the combination of ionone ketone terpene, a cetylpridinium and zinc salt, as described in U.S. Pat. No. 6,723,305, which is hereby incorporated by reference in its entirety. Accordingly, in some embodiments, the mouthwash composition does not contain a composition disclosed in U.S. Pat. No. 6,723,305, which is hereby incorporated herein by reference in its entirety.

In one embodiment, a mouthwash consumer product is provided, and the mouthwash consumer product does not include isomalt and a remineralization enhancing ingredient, as described in U.S. Pat. No. 7,300,645, which is hereby incorporated by reference in its entirety. Accordingly, in some embodiments, the mouthwash composition does not contain a composition disclosed in U.S. Pat. No. 47,300,645, which is hereby incorporated herein by reference in its entirety.

In one embodiment, a mouthwash consumer product is provided, and the mouthwash consumer product does not include compounds of the Formula VIII:

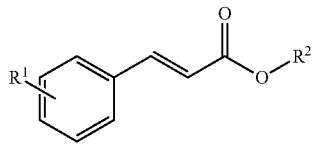

wherein $R^1$ and $R^2$ are defined according col. 4, lines 38-44 of U.S. Pat. No. 7,332,462, which is hereby incorporated by reference in its entirety. In another embodiment, the mouthwash consumer product does not include a liphatic alpha unsaturated dicarboxylic ester wherein the double bonds are bracketed between carbonyl groups, cycloalkyl tertiary alcohols, esters of alpha-, beta-, unsaturated monocarboxylic acids, and 4-cyclohexyl4-methyl-2-pentanone, also as described in U.S. Pat. No. 7,332,462. In another embodiment, the mouthwash consumer product does include a liphatic alpha unsaturated dicarboxylic ester wherein the double bonds are bracketed between carbonyl groups, cycloalkyl tertiary alcohols, esters of alpha-, beta-, unsaturated monocarboxylic acids, and 4-cyclohexyl4-methyl-2-pentanone. Accordingly, in some embodiments, the mouthwash composition does not contain a composition disclosed in U.S. Pat. No. 7,332,462, which is hereby incorporated herein by reference in its entirety.

In one embodiment, the consumer product is not a perfume or fragrance composition. In one embodiment, the consumer product is not a dental floss.

In one embodiment, the consumer product does not include a malodor eliminating composition having an odor intensity less than that of a 10% solution of benzyl acetate in dipropylene glycol, as described in EP 0 404 470, which is incorporated herein by reference in its entirety. Accordingly, in some embodiments, the mouthwash composition does not contain a composition disclosed in EP 0 404 470, which is hereby incorporated herein by reference in its entirety.

In one embodiment, a mouthwash consumer product is provided, and the mouthwash consumer product does not include a compound of the Formula IX:

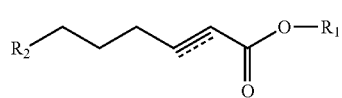

wherein $R_1$ is a residue selected from the group consisting of $CH_3$ or $CH_2CH_3$;

$R_2$ is a residue selected from the group consisting of H, $CH_3$, $CH_2CH_3$, $CH_2CH_2CH_3$; and the double bond with dashed line as shown is a double bond or a triple bond.

as described at U.S. Patent Application Publication 20080311054, which is incorporated herein by reference in its entirety. Accordingly, in some embodiments, the mouthwash composition does not contain a composition disclosed in U.S. Patent Application Publication 20080311054, which is hereby incorporated herein by reference in its entirety.

In one embodiment, a mouthwash consumer product is provided, and the mouthwash consumer product does not include a compound represented by the Formula X:

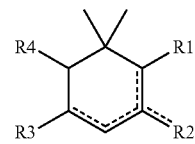

wherein $R_1$-$R_4$ are defined in page 4 of WO2008/026140, which is hereby incorporated in its entirety. Accordingly, in some embodiments, the mouthwash composition does not contain a composition disclosed in International Published Application No. WO2008/026140, which is hereby incorporated herein by reference in its entirety.

The disclosed malodor eliminating compositions, and end products containing the same, can further include additional flavor ingredients and excipients well known in the art. Examples of known flavor ingredient can be found in FEMA (Flavor and Extracts Manufacturers Association of the United States) publications, particularly those compounds generally recognized as safe (FEMA-GRAS materials). Malodor eliminating compositions of the present invention may further include one or more components described in Allured's Flavor and Fragrance materials 2004, published by Allured Publishing Inc., and hereby incorporated by reference.

In one embodiment, the disclosed malodor eliminating compositions are combined with zinc salt, stannous salt, baking soda, a polyphenol, an essential oil, and/or an anti bacterial agent, e.g., quaternary ammonium, cethylpyridinium chloride, cyclohexidine, trichlosan, and antibacterial flavor materials of the like.

The disclosed malodor eliminating compositions can be used in various oral care end products including, for example, a toothpaste or gel, a mouthwash, a mouth spray, a confection (e.g. a hard or soft candy), a breath mint, a dissolvable breath strip, a chewing gum, a lozenge, or a pharmaceutical or medicinal products (e.g. pharmaceutical products suitable for buccal administration).

The malodor eliminating compositions according to the invention can be in the form of a simple mixture of odor eliminating compounds or can be in an encapsulated form, e.g., malodor eliminating compound(s) entrapped in a solid matrix that may include wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, malitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate and mixtures thereof. Encapsulation techniques are well-known to persons skilled in the art, and may be performed, for instance, using techniques such as spray-drying, agglomeration or extrusion, or coating encapsulation, including coacervation and complex coacervation techniques.

When a malodor eliminating composition of the present invention is incorporated in a chewing or bubble gum, the end product will typically include one or more gum bases and other standard components such as flavoring agents, softeners, sweeteners and the like. Flavoring agents for use in chewing gum compositions are well known and include natural flavors such as citrus oils, peppermint oil, spearmint oil, oil of wintergreen, cinnamon, ginger and the like; and artificial flavors such as carvone, limonene, cinnamic aldehyde, linalool, geraniol, ethyl butyrate, and the like. Suitable sweeteners include natural and artificial sweetening agents, including sugar and sugarless varieties, and are typically present in the chewing gum in amounts of from about 20% to 80% by weight, preferably from about 30% to 60% by weight, based on the total weight of the chewing gum consumer product. Sugarless sweeteners include, but are not limited to, sugar alcohols such as sorbitol, mannitol, xylitol, hydrogenated starch hydrolysates, malitol, and the like. High intensity sweeteners such as sucralose, aspartame, neotame, salts of acesulfame, and the like, when employed, are typically present up to about 1.0% by weight of the chewing gum consumer product.

In an alternative embodiment, a malodor eliminating composition of the present invention is included in an oral personal care product (e.g., a mouthwash or toothpaste). As is known in the art, a mouthwash can be prepared by a) dissolving a malodor eliminating composition (present in liquid or powder form) in a solvent (e.g., water) that further includes, for example, a flavor such as menthol and a surfactant; and then mixing the resulting solution with, for example, an aqueous erythritol solution.

EXAMPLES

The present application is further described by means of the examples, presented below, wherein the abbreviations have the usual meaning in the art.

Methyl mercaptan is one of the major oral malodor materials. Propyl and allyl mercaptan were found in the headspace of *Allium* sp. (onion, garlic). See Laakso, I., et al., *Planta Med.* 1989, 55(3) 257-61; Tokitomo, Y., Kobayashi, A., *Biosci. Biotech. Biochem.*, 1992, 56(11)1865-66. Propyl mercaptan was also reported to be released from the precursor, S-propyl-L-cysteine in the mouth after eating onion (see Starkenmann, C, et al., *J. Agric. Food Chem.* 2008, (56) 9575-80). Methyl and allyl mercaptan, allylmethylsulfide were found in human breath after garlic ingestion (see Suarez, F., et al., *Am. J. Physiol.*, 1992, 276(2, Part 1) G425-30). Furfuryl mercaptan was used as coffee malodor material. As described in the following Examples, such mercaptan compounds were used as test malodor materials.

The use of such examples is illustrative only and in no way limits the scope and meaning of the invention or of any exemplified term used herein. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Methyl Mercaptan Chemical Suppression by Group A and Group B Compounds

2 µl of 0.5%(w/v) of sodium methoxide in deionized water, 20 µl of 1% (w/v) test malodor eliminating material in ethanol, 80 µl of ethanol, and 900 µl of deionized water were added into a 2 ml GC vial, left to sit at room temperature for 2 hours, and analyzed using Multipurpose sampler-GC-PFPD (Gas Chromatography-Pulsed Flame Photometric Detector) (GC-PFPD)MPS2 (Gerstel)—GC; 6890N (Agilent)—PFPD; model 5380 (OI Analytical). As a control, ethanol was added instead of test malodor eliminating materials. The final concentration of test OE material and malodor material are 200 ppm and 10 ppmm, respectively. Malodor suppression was calculated as follows: Malodor Suppression (%)=(GC area of control sample−GC area of test_sample)/GC area of control sample×100

TABLE 1

Methyl Mercaptan Suppression by Malodor Eliminating Materials

| Group | Compound | ClogP | methyl mercaptan suppression (%) |
|---|---|---|---|
| Group A | AMYL CINN ALD, ALPHA | 4.474 | 5 |
| | CARVONE-L | 2.465 | 14 |
| | CINN ALD | 2.049 | 33 |
| | CITRAL SYN REFINED (FDO) | 2.950 | 25 |
| | DAMASCENONE | 4.266 | 100 |
| | DAMASCONE, BETA | 4.690 | 99 |
| | DECENAL, TRANS-2, | 3.694 | 90 |
| | DODECENAL, TRANS-2, | 4.752 | 53 |
| | ETH CINNMATE | 2.994 | 50 |
| | ETHYL-TRANS-2 BUTENOATE | 1.855 | 73 |
| | HEPTADIENAL, TRANS-2-TRANS-4 | 1.683 | 44 |
| | HEPTENAL-TRANS-2 | 2.107 | 82 |

TABLE 1-continued

Methyl Mercaptan Suppression by Malodor Eliminating Materials

| Group | Compound | ClogP | methyl mercaptan suppression (%) |
|---|---|---|---|
| | HEXENAL, TRANS-2, | 1.578 | 82 |
| | IONONE-ALPHA | 3.710 | 14 |
| | IONONE-BETA | 3.710 | 23 |
| | ISO JASMONE | 3.136 | 31 |
| | ISOAMYL CINNAMATE | 4.451 | 10 |
| | ISOPHORONE | 2.088 | 31 |
| | ISOPROPYL CINNAMATE | 3.303 | 21 |
| | JASMONE, CIS | 2.642 | 32 |
| | METH 2-PHEN 2-HEXENAL, 5, | 3.665 | 59 |
| | METH CINNAMATE | 2.465 | 36 |
| | METHYL HEPTIN CARE | 2.718 | 92 |
| | NONADIEN-1-AL, TRANS-2, CIS-6, | 2.681 | 74 |
| | NONADIENAL-TRANS-2-TRANS-4 | 2.741 | 42 |
| | NONENAL, TRANS-2, | 3.165 | 86 |
| | OCTENAL TRANS-2 | 2.636 | 82 |
| | PERILLA ALD | 2.456 | 12 |
| | PIPERITONE D | 2.497 | 37 |
| Group B | EUGENOL | 2.397 | 46 |
| | HEXENOL, CIS-3- | 1.397 | 30 |
| | HEXENYL BUTY, CIS-3, | 3.401 | 22 |
| | HEXENYL CIS 3 ACETATE | 2.343 | 60 |
| | HEXENYL ISO VAL, CIS-3, | 3.800 | 24 |
| | HEXENYL PROP, CIS-3, | 2.872 | 32 |
| | HEXENOL, TRANS-2- | 1.597 | 29 |
| | HEXENYL-TRANS-2 ACETATE | 2.543 | 35 |
| | ISOEUGENOL | 2.577 | 15 |
| | METHYL-3 -NONENOATE | 3.601 | 36 |
| | NONENOL, CIS 6 | 2.984 | 22 |
| | OCTEN-1 3-OL | 2.435 | 19 |

Example 2

Propyl, Allyl, Furfuryl Mercaptan Chemical Suppression by Malodor Eliminating Materials The selected OE materials were tested for propyl, allyl, and furfuryl mercaptan suppression. 100 µl of 0.01%(w/v) of test malodor material in ethanol, 2 µl of neat flavor oil and 900 µl of deionized water were added into a 4 ml vial and left to sit at room temperature for 2 hours. As a control, ethanol was added instead of test flavor materials. The final concentration of test OE material and malodor material are 0.2% and 10 ppm, respectively. 3 ml of ethanol was added into the resulting vial and the thiol level was analyzed using GC-PFPD. Each material was tested in triplicate. Malodor suppression was calculated as described in the example 1 above.

TABLE 2

Suppression of Certain Mercaptan Compounds by OE Materials

| malodor eliminating material | Malodor reduction (%) | | |
|---|---|---|---|
| | propyl mercaptan | allyl mercaptan | furfuryl mercaptan |
| CARVONE-L | <20 | <20 | 27 |
| CINN ALD | 26 | <20 | 27 |
| DAMASCENONE | 49 | 67 | 67 |
| DAMASCONE, BETA | 23 | 85 | 47 |
| EUGENOL | 44 | 63 | 80 |
| HEXENOL, CIS-3- | <20 | 53 | 58 |
| HEXENYL CIS 3 ACETATE | <20 | <20 | 28 |
| IONONE-ALPHA | <20 | 43 | 46 |
| IONONE-BETA | 27 | 37 | 51 |
| METHYL HEP CARB | 44 | 63 | 69 |
| PIPERITONED | <20 | 51 | 64 |

Example 3

Examination of Reaction Product of an OE Material and a Malodor Material

To examine the chemical reaction between OE material and malodor material, the selected OE materials, either damascenone or methyl heptin carbonate was mixed with methyl mercaptan. 100 µl of 0.01% of sodium thiomethoxide in deionized water, 2 µl of neat oil, and 900 µl of deionized water were mixed. After 2 hours, 3 ml of ethanol was added into the resulting vial and analyzed using Gas Chromatography-Pulsed Flame Photometric Detector (GC-PFPD). The adduct peaks, which was identified using Gas Chromatography-Mass Selective Detector (GC-MSD), were found in both mixture.

The results are shown in FIG. 1.

Example 4

Methyl Mercaptan Suppression by Group A and Group B Materials

The synergistic or additive activity of methyl mercaptan inhibition of malodor eliminating materials was tested. 5-40 µl of 1% (w/v) test OE materials in ethanol was placed into a 2 ml GC vial. Ethanol was added into this vial up to 1000 µl. 2 µl of 0.5%(w/v) of sodium methoxide in deionized water was added into the resulting vial, left to sit at room temperature for 2 hours, and analyzed using Multipurpose sampler-GC-PFPD. As a control, ethanol was added instead of test OE materials. Malodor suppression was calculated as described in Example 1 above.

The following results were obtained:

TABLE 3

| Group A | | Group B | | methyl mercaptan suppression (%) | | | |
|---|---|---|---|---|---|---|---|
| name | level (ppm) | name | level (ppm) | A alone | B alone | theoretical additive effect (A + B) | A + B combination |
| DAMASCENONE | 50 | HEXENYL CIS 3 ACETATE | 100 | 17 | 22 | 39 | 38 |
| METHYL HEP CARB | 50 | HEXENYL CIS 3 ACETATE | 100 | 53 | 22 | 75 | 69 |
| IONONE-BETA | 200 | HEXENYL CIS 3 ACETATE | 100 | 71 | 22 | 93 | 73 |
| CINN ALD | 200 | HEXENYL CIS 3 ACETATE | 100 | −31 | 22 | −8 | −7 |
| ETH CINNNAMTE | 200 | HEXENYL CIS 3 ACETATE | 100 | 12 | 22 | 34 | 36 |

TABLE 3-continued

| | | | | | methyl mercaptan suppression (%) | |
|---|---|---|---|---|---|---|
| Group A | | Group B | | | | theoretical additive |
| name | level (ppm) | name | level (ppm) | A alone | B alone | effect (A + B) | A + B combination |
| HEXENAL, TRANS-2, | 200 | HEXENYL CIS 3 ACETATE | 100 | 10 | 22 | 32 | 33 |
| ETH DECADIENOATE | 200 | HEXENYL CIS 3 ACETATE | 100 | 7 | 27 | 34 | 34 |
| PIPERITONE D | 200 | HEXENYL CIS 3 ACETATE | 100 | 8 | 22 | 30 | 29 |
| ETHYL-TRANS-2 BUTENOATE | 200 | HEXENYL CIS 3 ACETATE | 100 | 64 | 27 | 91 | 72 |
| PHEN ETH TIGLATE | 200 | HEXENYL CIS 3 ACETATE | 100 | 4 | 27 | 31 | 27 |
| METHYL HEPTADIENONE | 200 | HEXENYL CIS 3 ACETATE | 100 | 12 | 27 | 39 | 27 |
| DAMASCENONE | 50 | EUGENOL | 400 | 28 | 12 | 40 | 42 |
| CINN ALD | 200 | EUGENOL | 400 | −8 | 12 | 4 | 29 |
| ETH CINNNAMTE | 200 | EUGENOL | 400 | 8 | 12 | 20 | 22 |
| HEXENAL, TRANS-2, | 200 | EUGENOL | 400 | 34 | 12 | 46 | 90 |
| METHYL HEP CARB | 50 | EUGENOL | 400 | 67 | 12 | 79 | 49 |
| ETH DECADIENOATE | 200 | EUGENOL | 400 | 21 | 12 | 33 | 25 |
| METHYL HEPTADIENONE | 200 | EUGENOL | 400 | 6 | 12 | 18 | 35 |
| PIPERITONED | 200 | EUGENOL | 400 | 12 | 12 | 24 | 24 |
| DAMASCENONE | 50 | HEXENOL, CIS-3- | 400 | 28 | 32 | 60 | 46 |
| CINN ALD | 200 | HEXENOL, CIS-3- | 400 | −12 | 32 | 20 | 9 |
| ETH CINNNAMTE | 200 | HEXENOL, CIS-3- | 400 | 8 | 32 | 40 | 38 |
| HEXENAL, TRANS-2, | 200 | HEXENOL, CIS-3- | 400 | 34 | 32 | 66 | 44 |
| METHYL HEP CARB | 50 | HEXENOL, CIS-3- | 400 | 67 | 32 | 99 | 76 |
| ETH DECADIENOATE | 200 | HEXENOL, CIS-3- | 400 | 21 | 32 | 53 | 44 |
| METHYL HEPTADIENONE | 200 | HEXENOL, CIS-3- | 400 | 8 | 32 | 40 | 35 |
| PIPERITONED | 200 | HEXENOL, CIS-3- | 400 | 12 | 32 | 44 | 39 |
| CINN ALD | 200 | THYMOL | 400 | −3 | 0 | −3 | 5 |
| METHYL HEPTADIENONE | 200 | THYMOL | 400 | 15 | 0 | 15 | 14 |
| HEXENAL, TRANS-2, | 200 | THYMOL | 400 | 28 | 0 | 28 | 69 |
| AMYL CINN ALD, ALPHA | 200 | EUGENOL | 400 | −3 | 14 | 11 | 16 |
| CITRAL SYN REFINED (FDO) | 200 | EUGENOL | 400 | 1 | 15 | 16 | 27 |
| CARVONE-L | 200 | EUGENOL | 400 | 12 | 14 | 26 | 27 |
| PERILLA ALD | 200 | EUGENOL | 400 | 16 | 14 | 30 | 30 |
| METHYL 3 NONENOATE | 200 | EUGENOL | 400 | 7 | 14 | 21 | 22 |
| AMYL CINN ALD, ALPHA | 200 | EUGENOL | 400 | −1 | 16 | 15 | 17 |
| CITRAL SYN REFINED (FDO) | 200 | EUGENOL | 400 | 0 | 16 | 16 | 29 |
| CUMIN ALD | 200 | EUGENOL | 400 | −42 | 16 | −26 | 28 |
| BENZ ALD | 200 | EUGENOL | 400 | 4 | 16 | 20 | 18 |
| ANIS ALD | 200 | EUGENOL | 400 | 5 | 16 | 21 | 20 |
| ACETOPHENONE | 200 | EUGENOL | 400 | 4 | 16 | 20 | 36 |
| HEXENAL, TRANS-2 | 200 | PROPYLENE GLYCOL (SOLVENT) | 400 | 33 | −5 | 27 | 44 |

Example 5

Allyl Mercaptan Suppression by Malodor Eliminating Materials

Allyl mercaptan inhibition by malodor eliminating materials was tested. 10 μl each of 1% (w/v) test OE materials in ethanol was added in to a 2 ml GC vial. Ethanol and 800 μl of deionized water were added into this vial. The total ethanol level is 200 μl. 10 μl of 0.1%(w/v) of allyl mercaptan in deionized water was added into the GC vial. The resulting vials were left to sit at room temperature for 2 hours, and analyzed using Multipurpose sampler-GC-PFPD. As a control, ethanol was added instead of test OE materials. Malodor suppression was calculated as described in the example 1 above.

Figure 2:
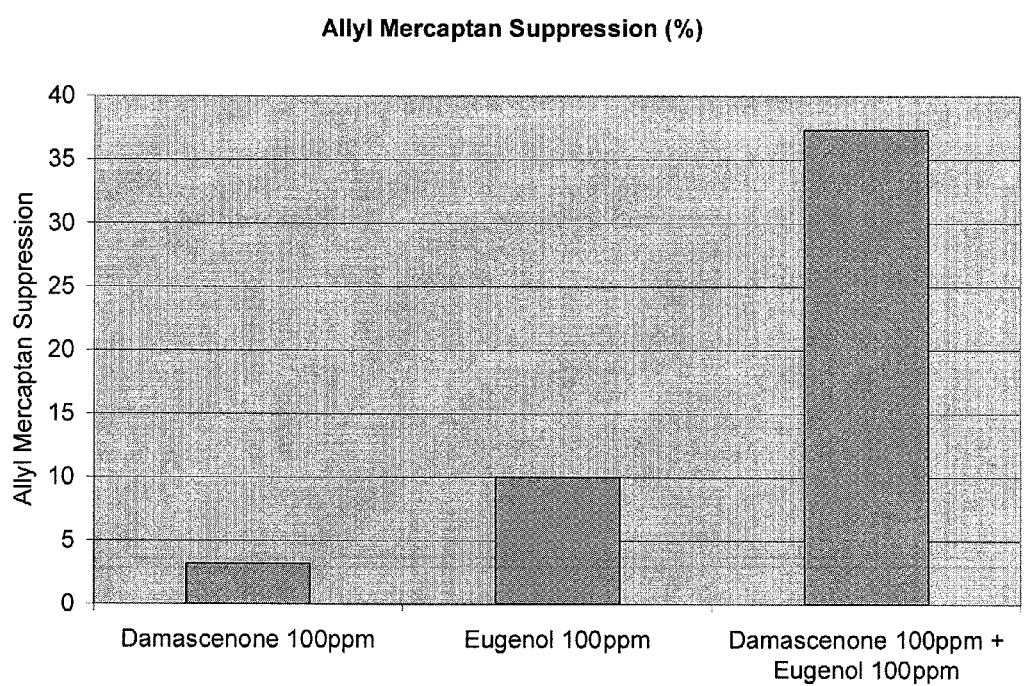
FIG. 2 illustrates malodor suppression using a combination of malodor eliminating compounds according to some embodiments of the disclosed subject matter.

Surprisingly and unexpectedly, as shown in FIG. 2, the combination of damascenone and eugenol showed remarkably higher malodor suppression effect than each single material.

Example 6

Preparation of Malodor Suppression Flavor

The following compound including the malodor eliminating materials were mixed and thus a malodor suppression flavor was obtained.

TABLE 4

| Flavor A (melon-cuke flavor) | |
|---|---|
| Compound | wt % |
| Menthol Natural | 30.00 |
| Dodecalactone Delta | 0.50 |
| Decalactone Delta | 0.50 |
| Ethyl Acetate | 2.00 |
| Hexenol-Trans-2 | 0.10 |
| Ionone Alpha Nat (90%) 1% in EtOH | 0.05 |
| Ionone Beta Nat (90%) 1% in EtOH | 0.45 |
| Phenyl Ethyl Propionate | 0.15 |
| Phenyl Ethyl Alcohol-beta | 0.20 |

TABLE 4-continued

Flavor A (melon-cuke flavor)

| Compound | wt % |
|---|---|
| Ethyl 2-Methylbutyrate | 1.50 |
| Ethyl Butyrate | 5.00 |
| Undecalactone Gamma/aldc14S OCL | 1.00 |
| Cyclopentadecanolide 1% in Natural EtOH | 0.25 |
| Damascenone | 0.40 |
| Damascone Beta | 0.40 |
| Eugenol | 0.40 |
| Cinnamic Aldehyde | 0.40 |
| Piperitone-D | 1.60 |
| Cis-3-Hexenol | 6.00 |
| Cis-3-Hexenyl Acetate | 6.00 |
| Methyl Heptin Carbonate | 3.60 |
| Carvone-L | 0.80 |
| Propylene Glycol Tincture | 38.70 |
| Total | 100.00 |

TABLE 5

Flavor B (Spice mint flavor)

| Compound | wt % |
|---|---|
| Menthol Natural | 40.00 |
| Anethol NF | 10.00 |
| Nat & Art Peppermint oil plus | 10.00 |
| Eugenol | 6.00 |
| Cinnamic Aldehyde | 9.00 |
| Piperitone-D | 2.40 |
| Carvone-L | 0.60 |
| Damascenone | 0.30 |
| Damascone Beta | 0.60 |
| Ionone-Beta in Triacetin 1% | 3.00 |
| Triglycerides Dist. Medchain Nat | 18.10 |
| Total | 100.00 |

TABLE 6

Flavor C (Fruit flavor)

| Compound | wt % |
|---|---|
| Ethyl-t-2-Butenoate | 5.00 |
| Trans-2-Hexenal | 12.50 |
| Damascenone 1.0% in Triac | 15.00 |
| Damascone B 10% in Triac | 12.50 |
| cis-3-Hexenyl acetate | 33.80 |
| C is-3 -Hexenol | 10.00 |
| Nonadienal T-2, C-6, 1% Triac | 5.00 |
| Eugenol | 1.20 |
| Methyl Heptine Carbonate | 5.00 |
| Total | 100.00 |

TABLE 7

Flavor D (Sweet spice flavor)

| Compound | wt % |
|---|---|
| Ethyl-t-2-Butenoate | 2.00 |
| Damascenone | 2.40 |
| Damascone B | 2.00 |
| Eugenol | 40.00 |
| Cinnamic Aldehyde | 40.00 |
| Ethyl Cinnamate | 8.00 |
| Methyl Cinnamate | 5.60 |
| Total | 100.00 |

TABLE 8

| Compound | wt % |
|---|---|
| Non-Active Flavor E (fruit flavor) | |
| Decalactone-Gamma | 0.5 |
| Dodecalactone-Gamma | 0.5 |
| Ethyl Acetate | 4.0 |
| Hexenol-Trans-2 | 0.2 |
| Phenethyl Propionate | 0.3 |
| Phenyl Ethyl Alcohol-Beta | 0.4 |
| Ethyl 2-Methylbutyrate | 3.0 |
| Ethyl butyrate | 10 |
| Undecalactone, Gamma | 2.0 |
| Damascone Beta 1% in ETOH | 0.5 |
| Damascenone 1% in ETOH | 1 |
| Ionone Alpha Nat 1% in ETOH | 0.1 |
| Ionone Beta Nat 90% in ETOH | 0.1 |
| Cyclopentadecanolide 1% in Natural ETOH | 0.5 |
| Hexenyl-Cis-3 Acetate Nat 10% in ETOH | 0.2 |
| Propylene Glycol Tincture | 76.7 |
| Total | 100.00 |
| Non-Active Flavor F | |
| Ethyl Butyrate | 20.00 |
| Ethyl Acetate | 8.00 |
| Spearmint Oil FWN | 4.00 |
| Ethyl Maltol | 4.00 |
| Ionone Alpha 1% in triac | 0.20 |
| Phenyl Ethyl Alcohol | 2.00 |
| Anisyl Acetate | 12.00 |
| IsoAmyl IsoValerate | 4.00 |
| Allyl Caproate | 2.00 |
| IsoAmyl Acetate | 3.80 |
| Benzaldehyde | 40.00 |
| Total | 100.00 |

Example 7

Chemical Malodor Suppression by Malodor Suppression Flavor

Flavors A, B, and non-active flavor E all of Example 6 were tested. For methyl mercaptan suppression tests, 100 µl of 0.01% of sodium thiomethoxide in deionized water, 2 µl of neat oil, 100 µl of ethanol and 800 µl of deionized water were added into a 4 ml vial and left to sit at room temperature for 2 hours. For propyl, allyl and furfuryl mercaptan suppression tests 100 µl of 0.01%(w/v) of test malodor material in ethanol, 2 µl of neat flavor oil and 900 µl of deionized water were added into a 4 ml vial and left to sit at room temperature for 2 hours.

3 ml of ethanol was added into the resulting vial and the thiol level was analyzed using GC-PFPD. As a control, ethanol was added instead of test flavor materials.

Figure 3:
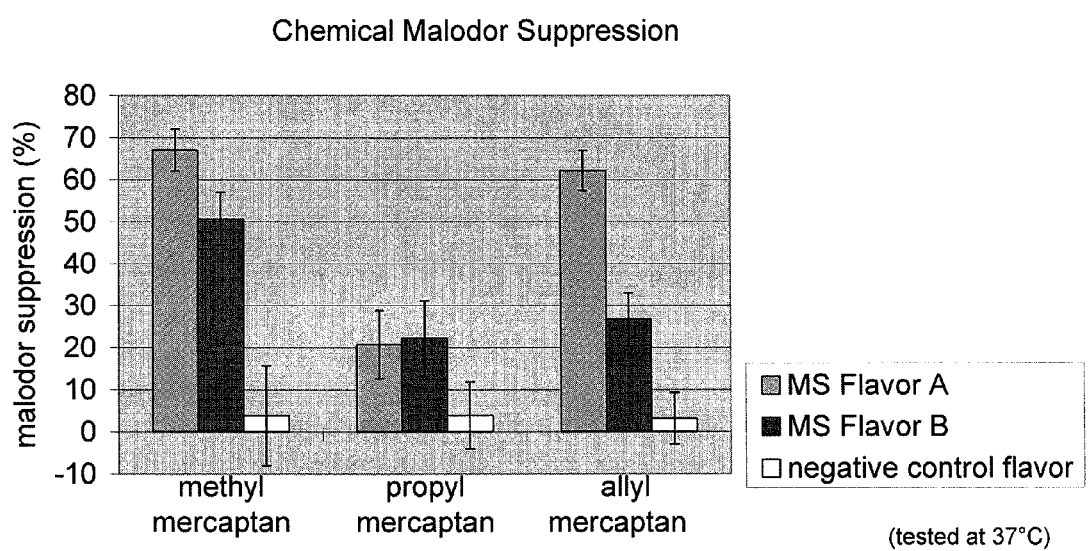
FIG. 3 illustrates malodor suppression by certain malodor eliminating compositions according to some embodiments of the disclosed subject matter.

As shown in FIG. 3, both Flavor A and B chemically suppressed the mercaptan level while the negative control, Not-Active Flavor E, did not show reduction.

Example 8

Chemical Malodor Suppression by Malodor Suppression Flavor

2 µl of 0.5%(w/v) of sodium methoxide in deionized water, 20 µl of 1% (w/v) test flavor in ethanol, 80 µl of ethanol, and 900 µl of deionized water were added into a 2 ml GC vial, left to sit at room temperature for 2 hours, and analyzed using Multipurpose sampler-GC-PFPD. As a control, ethanol was added instead of test OE materials. The final concentration of test flavor and malodor material are 200 ppm and 10 ppmm, respectively. Malodor suppression was calculated as follows: Malodor Suppression (%)=(GC area of control sample−GC area of test_sample)/GC area of control sample×100.

Figure 4:
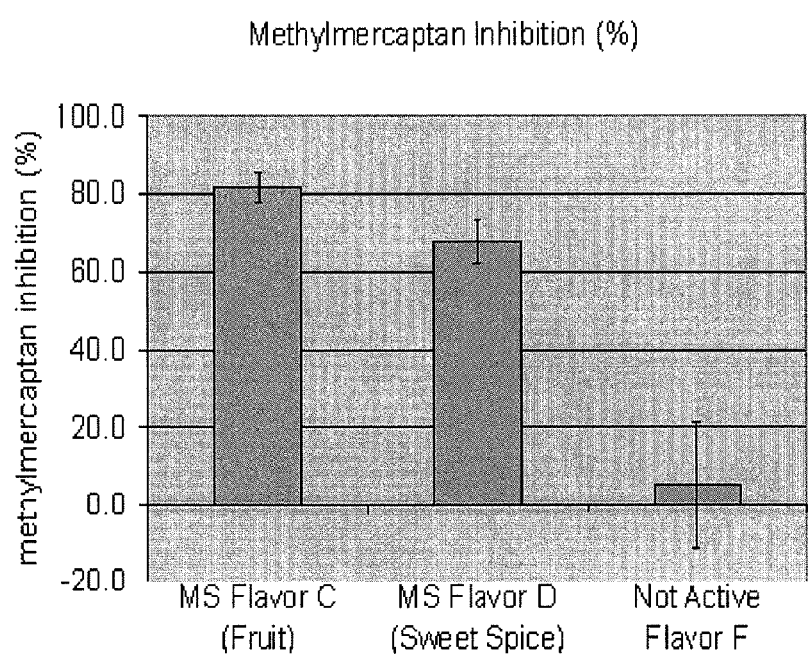
FIG. 4 illustrates malodor suppression by certain malodor eliminating compositions according to some embodiments of the disclosed subject matter.

As shown in FIG. 4, both MS Flavor C and D chemically suppressed the mercaptan level while the negative control, Not-Active Flavor F, did not show reduction.

Example 9

Olfactory Jar Test of Malodor Suppression Flavor

100 μl of 0.01% malodor material (w/w) in deionized water or propylene glycol and 100 of 1% Flavor A in propylene glycol (w/w) were applied onto the solid support (4 cm×4 cm of cotton fabric) in a 2 oz (60 mL) jar. After 30 minutes 8-11 volunteers (age 30-55) sniffed and scored malodor strength (0; no odor to 5; extremely foul odor) and pleasantness (0; unpleasant to 5; very pleasant).

Figure 5A:
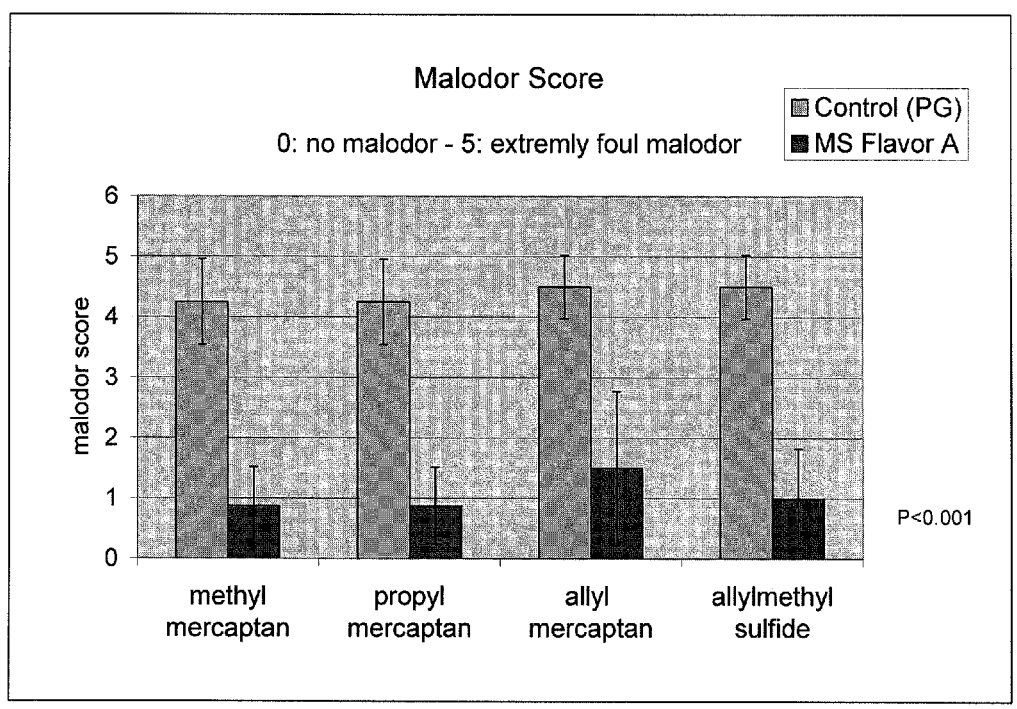
FIGS. 5A and 5B illustrate malodor suppression by malodor eliminating compositions according to some embodiments of the disclosed subject matter.
Figure 5B:
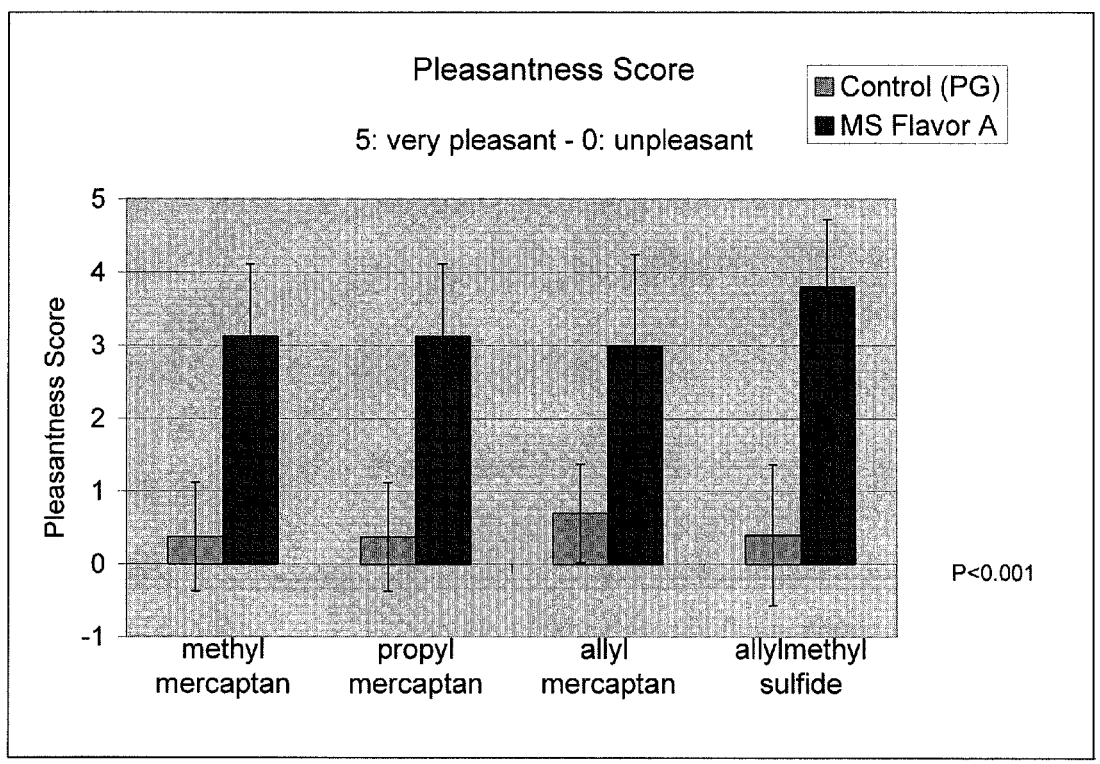

As shown in FIGS. 5A and 5B, Flavor A significantly suppressed malodor perception and showed a better pleasantness score ($P<0.001$).

Example 10

Preparation of Mouthrinse Containing Malodor Suppression Flavor

The following compound including the malodor suppression flavor C or D prepared in Example 6 were mixed and thus a mouth rinsing solution was obtained by commonly employed methods. As a control, a mouthrinse without flavor was prepared.

TABLE 9

| Composition of mouthrinse G, H, I (Wt. %) | | | |
|---|---|---|---|
| | Mouthrinse G (with Flavor C) | Mouthrinse H (with Flavor D) | Mouthrinse I (w/o flavor) |
| glycerin | 10.00 | 10.00 | 10.00 |
| Sucralose ™ 25% | 0.20 | 0.20 | 0.20 |
| Ethanol 95% | 8.00 | 8.00 | 8.00 |
| Flavor | 0.15 (MS Flavor C) | 0.15 (MS Flavor D) | 0.00 |
| Water | 81.65 | 81.65 | 81.80 |
| Total | 100.00 | 100.00 | 100.00 |

Example 11

The Suppression of Malodor Produced from Saliva by Mouthrinse

Saliva was collected in the morning from one healthy volunteer before eating, drinking, or brushing teeth. The saliva was stored in ice water or in the refrigerator before the experiment. 10 μl of mouthrinse in Example 10 (Mouthrinses G, Mouthrinse H and Mouthrinse I) and 490 μl of saliva were placed into 20 ml headspace vial. As a blank control, no mouthrinse was added. The resulted headspace vial was filled with nitrogen gas, crimped with crimp cap, incubated at 37° C. for 20 hours. After incubation, each vial was kept at 4-6° C. in the refrigerator or in the agitator of multipurpose sampler until the GC analysis began. Sulfur level in the headspace was analyzed using SPME (Car/PDMS 5 minutes)-GC-PFPD.

Figure 6:
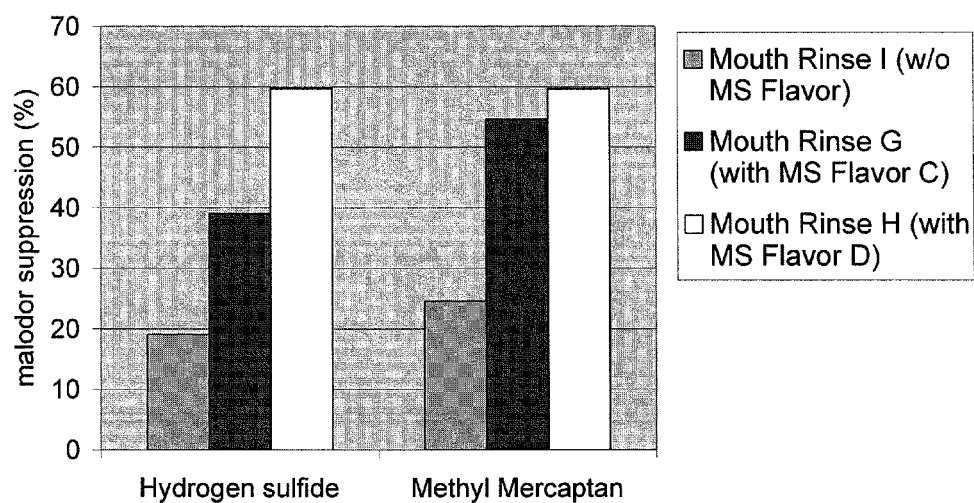
FIG. 6 illustrates malodor suppression by a mouthrinse composition according to some embodiments of the disclosed subject matter.

As shown in FIG. 6, the mouthrinse containing MS Flavor C, and D showed higher malodor suppression.

Example 12

The Suppression of Methyl Mercaptan

100 μl of 0.01%(w/v) of test malodor material in ethanol, 2 μl of neat flavor oil and 900 μl of deionized water were added into a 4 ml vial and left to sit at room temperature for 2 hours. As a control, ethanol was added instead of the malodor reducing compound. The final concentration of test material and malodor material are 0.2% and 10 ppmm, respectively. 3 ml of ethanol was added into the resulting vial and the thiol level was analyzed using GC-PFPD as described above. Each material was tested in triplicate. Malodor suppression was calculated as described in the example 1 above.

| NAME | methyl mercaptan suppression (%) |
|---|---|
| ANETHOL NF | <20 |
| CARVONE L | 60 |
| CINNAMIC ALDEHYDE | 26 |
| CYCLOPENTADECANOLIDE | <20 |
| DAMACENONE | 81 |
| DAMASCONE BETA | 74 |
| DECALACTONE DELTA | <20 |
| DODECALACTONE DELTA | <20 |
| ETHYL 2-METHYLBUTYRATE | <20 |
| ETHYL ACETATE | <20 |
| ETHYL BUTYRATE | <20 |
| EUGENOL | 78 |
| HEXENOL-CIS-3 | 51 |
| HEXENYL-CIS-3 ACETATE | 38 |
| IONONE ALPHA | 50 |
| IONONE BETA | 55 |
| MELONAL | <20 |
| MENTHOL NATURAL | <20 |
| MENTHYL ACETATE | <20 |
| METHYL HEPTINE CARBONATE | 80 |
| METHYL HEPTYL KETONE | <20 |
| METHYL SALICYLATE EXT PURE | <20 |
| PEPERITONE-D | 45 |
| PHENYL ETHYL ALCOHOL-BETA | <20 |
| PHENYLETHYL PROPIONATE | <20 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of each of which is incorporated herein by reference in its entirety for all purposes.

The invention claimed is:

1. A malodor eliminating composition for an orally consumable end product, consisting essentially of:
    (a) at least one Group A eliminating compound selected from the group consisting of damascenone, damascone beta, trans-2-hexenal, citral, acetophenone, and combinations thereof;

(b) from about 0.001% to about 99% weight by weight of at least one Group B eliminating compound selected from the group consisting of eugenol, thymol, and combinations thereof;
(c) a diol solvent selected from the group consisting of 3-(1-menthoxy)propane-1,2-diol, p-menthane-3,8-diol, propylene glycol, and combinations thereof; and
(d) a malodor masking compound selected from the group consisting of ethyl butyl, menthol, anisyl acetate, ethyl acetate, phenethyl alcohol, ethyl 2-methyl butyrate, ethyl butyrate, citrus oils, peppermint oil, spearmint oil, oil of wintergreen, cinnamon, ginger, and combinations thereof,
wherein the composition does not contain a flavor enhancer or a polyphenol and wherein the at least one Group A and at least one Group B compounds are provided in synergistically effective amounts to eliminate malodor.

2. The composition of claim 1, wherein the Group A eliminating compound is present in an amount of from about 20% to about 95% weight by weight in the composition.

3. The composition of claim 1, wherein the Group A eliminating compound is present in an amount of from about 7.2% to about 95% weight by weight in the composition.

4. The composition of claim 1, wherein the Group B eliminating compound is present in an amount of from about 2% to about 40% weight by weight in the composition.

5. The composition of claim 1, wherein the Group B eliminating compound is present in an amount of from about 2% to about 45% weight by weight in the composition.

6. The composition of claim 1, wherein the Group A eliminating compound is damascenone.

7. The composition of claim 6, wherein the damascenone is selected from the group consisting of damascenone alpha, damascenone beta, and combinations thereof.

8. The composition of claim 6, wherein the Group B eliminating compound is eugenol.

9. The composition of claim 6, wherein the Group B eliminating compound is thymol.

10. The composition of claim 1, wherein the Group A eliminating compound is damascone beta.

11. The composition of claim 10, wherein the Group B eliminating compound is eugenol.

12. The composition of claim 10, wherein the Group B eliminating compound is thymol.

13. The composition of claim 1, wherein the Group A eliminating compound is trans-2-hexenal.

14. The composition of claim 13, wherein the Group B eliminating compound is eugenol.

15. The composition of claim 13, wherein the Group B eliminating compound is thymol.

16. The composition of claim 1, wherein the Group A eliminating compound is citral.

17. The composition of claim 16, wherein the Group B eliminating compound is eugenol.

18. The composition of claim 1, wherein the Group A eliminating compound is acetophenone.

19. The composition of claim 18, wherein the Group B eliminating compound is eugenol.

* * * * *

UNITED STATES PATENT AND TRADEMARK OFFICE
CERTIFICATE OF CORRECTION

| | | |
|---|---|---|
| PATENT NO. | : 9,351,944 B1 | |
| APPLICATION NO. | : 12/615157 | |
| DATED | : May 31, 2016 | |
| INVENTOR(S) | : Akiko Yamasaki, James Buchanan and Michael John Munroe | |

It is certified that error appears in the above-identified patent and that said Letters Patent is hereby corrected as shown below:

IN THE CLAIMS:

At column 25 line 9:

"consisting of ethyl butyl, menthol, anisyl acetate, ethyl." should read

-- consisting of menthol, anisyl acetate, ethyl." --

Signed and Sealed this
Twelfth Day of July, 2016

Michelle K. Lee
*Director of the United States Patent and Trademark Office*

UNITED STATES PATENT AND TRADEMARK OFFICE
CERTIFICATE OF CORRECTION

PATENT NO. : 9,351,944 B1
APPLICATION NO. : 12/615157
DATED : May 31, 2016
INVENTOR(S) : Akiko Yamasaki, James Buchanan and Michael John Munroe Page 1 of 1

It is certified that error appears in the above-identified patent and that said Letters Patent is hereby corrected as shown below:

IN THE CLAIMS:

At column 25 line 9:

"consisting of ethyl butyl, menthol, anisyl acetate, ethyl." should read

-- consisting of menthol, anisyl acetate, ethyl" --

Signed and Sealed this
Sixteenth Day of August, 2016

Michelle K. Lee
*Director of the United States Patent and Trademark Office*